United States Patent [19]

Koebner

[11] 3,941,810
[45] Mar. 2, 1976

[54] SULFONATION OF AROMATIC COMPOUNDS IN THE PRESENCE OF SOLVENTS

[76] Inventor: Adolf Koebner, The Retreat, St. Bees, Cumberland, England

[22] Filed: Oct. 30, 1973

[21] Appl. No.: 411,053

[30] Foreign Application Priority Data
Oct. 30, 1972  United Kingdom............... 49928/72

[52] U.S. Cl....... 260/329 S; 260/505 C; 260/505 E; 260/512 R; 260/512 C
[51] Int. Cl.²............... C07D 333/00; C07C 143/24
[58] Field of Search......... 260/505 E, 505 C, 505 S, 260/512 R, 512 C, 329 S, 513 R

[56] References Cited
UNITED STATES PATENTS

| | | | |
|---|---|---|---|
| 2,616,936 | 11/1952 | Mammen et al. | 260/513 R |
| 2,704,295 | 3/1955 | Gilbert et al. | 260/505 E |
| 2,798,089 | 7/1957 | Norwood et al. | 260/505 E |
| 2,832,801 | 4/1958 | Berstein | 260/505 S |
| 3,232,976 | 2/1966 | Lohr | 260/505 S |
| 3,248,413 | 4/1966 | Motl | 260/505 S |
| 3,270,038 | 8/1966 | Marshall et al. | 260/505 S |
| 3,410,895 | 11/1968 | Graf et al. | 260/505 C |

*Primary Examiner*—James O. Thomas, Jr.
*Assistant Examiner*—Nicky Chan
*Attorney, Agent, or Firm*—Depaoli & O'Brien

[57] ABSTRACT

A process for the sulfonation of aromatic compounds wherein an aromatic substance consisting of one or more aromatic compounds susceptible to the action of sulfur trioxide is formed into a reactant by admixture with one or more organic liquids, substantially inert to sulfur trioxide under the conditions of the process, which reactant is brought to boiling at a temperature not greater than 100°C under a pressure of from 0.1 mm Hg to atmospheric pressure, gaseous sulfur trioxide is introduced thereinto thereby causing it to continue to boil, the component or components of the reactant thus volatilized is or are reconverted to liquid in a heat-exchanger and recycled to the reaction chamber, and the pressure in the reaction chamber and the rate at which the gaseous sulfur trioxide is introduced into the reactant are controlled so as to ensure that there is always present in the reaction chamber an amount of volatilizable matter exceeding that amount volatilizable by the heat of reaction of the aromatic substance present in the reaction chamber with the gaseous sulfur trioxide in contact with said aromatic substance and that the temperature of the reaction mixture is a temperature of 100°C or below.

4 Claims, 2 Drawing Figures

3,941,810

SULFONATION OF AROMATIC COMPOUNDS IN THE PRESENCE OF SOLVENTS

This invention concerns improvements in or relating to the sulfonation of aromatic compounds in the presence of solvents.

BACKGROUND OF THE INVENTION

As explained more fully in copending Application Ser. No. 411,054 entitled "Improvements in or relating to the sulfonation of aromatic compounds" of even date herewith, whose disclosure is incorporated herein by cross-reference, aromatic sulfonic acids, either as such or in the form of their salts with organic or inorganic bases, are widely used. Such aromatic sulfonic acids are usually prepared by reacting the corresponding unsulfonated aromatic compound with a sulfonating agent. In the past concentrated sulfuric acid has been the principle sulfonating agent employed, but oleum (which is a solution of sulfur trioxide in concentrated sulfuric acid) has also been used and in certain instances so too has sulfur trioxide itself.

However, the use of sulfuric acid always results in the production of water, which progressively dilutes the sulfuric acid employed, until its concentration becomes too low for it to effect sulfonation. Thus it will generally be necessary to employ a large excess of sulfuric acid over that theoretically needed, in order to effect a high conversion of the aromatic compound present into the corresponding sulfonic acid; but in that case, the end product is a mixture comprising the desired aromatic sulfonic acid, any unreacted aromatic compound, by-products of the reaction and excess sulfuric acid. The separation of these can be achieved only at some cost; and the substantial quantities of inorganic by-products (mainly sulfuric acid) can be disposed of only with difficulty, particularly now as effluent requirements become more stringent.

The use of oleum somewhat reduces these problems, since it is possible to use less oleum than sulfuric acid, but it will still normally be necessary to use an excess over that theoretically needed to react with the aromatic compound, and thus the problems of separating the desired sulfonic acid from the excess sulfuric acid and disposing of the latter still remain.

These problems can be more or less eliminated by using sulfur trioxide as the sulfonating agent. It reacts instantaneously with aromatic compounds, and it is not necessary to employ a substantial excess in order to achieve complete sulfonation. However, sulfur trioxide is very highly reactive, and its reactions with aromatic compounds are extremely exothermic and difficult to control; undesirable side reactions, particularly sulfone formation, often occur to a troublesome extent.

In attempts to overcome these drawbacks, and to moderate and control its reactions with aromatic compounds, the sulfur trioxide has been diluted with inert diluents before use. Two such procedures have been evolved; but one of them is only practicable for the sulfonation of hydrocarbons of high molecular weight (and thus very low vapor pressure at the reaction temperature) while the other is expensive to implement.

The first of these two known procedures using diluted sulfur trioxide involves diluting it with thoroughly dried air, to a concentration which is generally between 1 – 7% v/v; but this is unsuitable for sulfonating the more volatile aromatic compounds, since the amounts of such compounds entrained in the effluent air are so great as to be unacceptable, both from the point of view of cost and also because of the resultant toxicity hazards and fire and explosion risks, when the effluent air is discharged into the atmosphere — such effluent air cannot be recycled, due to its contamination with small droplets of organic matter and sulfuric acid. Moreover, the volume of air used is large, and the drying of large volumes of air is expensive.

The other of these two known procedures using diluted sulfur trioxide involves diluting it with a solvent inert to all the reactants, and in which the sulfur trioxide dissolves. This process is not restricted to the sulfonation of the less volatile aromatic compounds; but it is inevitably expensive, since the solvent must be recovered after the reaction is completed, and some losses are inevitable. Moreover in practice very few solvents are satisfactory, since a suitable solvent must be completely inert vis-a-vis the reactants, and not only must dissolve sulfur trioxide but also should preferably dissolve both the aromatic compound to be sulfonated and the aromatic sulfonic acid obtained from it. Liquid sulfur dioxide meets all these requirements and has been the solvent generally used commercially hitherto; but its use inevitably requires expensive pressure equipment, and refrigeration plant is necessary for its recovery. It will be apparent therefore, that the use of this process will normally only be commercially justified for the manufacture of sulfonates which sell at comparatively high prices.

A further process involving the direct reaction of sulfur trioxide with the aromatic compound has also been developed, and involves maintaining a reduced pressure or near-vacuum conditions in the reaction zone, thereby increasing the inter-molecular spacing of the sulfur trioxide and hence decreasing the rate of reaction. The sulfonation by this method has been described of alkyl benzenes having from 11 to 15 carbon atoms in the alkyl group, which compounds have a comparatively low vapor pressure at the sulfonation temperature. This procedure is however inapplicable to the sulfonation of aromatic compounds having a high vapor pressure at the sulfonation temperature, since when using such compounds the quantity of vapor sucked away to the vacuum pump (provided to reduce the pressure) would be unacceptably high. Moreover, this process requires continuous cycling of the reaction mixture through a heat-exchanger to keep its temperature from rising to a point where side-reactions would become unacceptable.

In the aforesaid co-pending application Ser. No. 411,054 of even date herewith, there is disclosed a process where sulfur trioxide is passed into the aromatic substance in the liquid state at its boiling point, normally under reduced pressure. The highly exothermic reaction between sulfur trioxide and the aromatic substance is controlled in the process, as the boiling of the aromatic substance effects thorough mixing, thereby minimizing the dangers of local overheating, and the heat of reaction is removed from the reaction chamber as the latent heat of volatilization of the aromatic substance. However, the process described in the aforesaid co-pending application Ser. No. 411,054 is only suitable for the sulfonation of aromatic substances which boil under a pressure of 0.1 mm Hg at 100°C or below. The sulfonation must be carried out at a temperature of 100°C or below, since above this temperature side-reactions and darkening of the product take place to a significant extent, and thus this process can be applied only to aromatic substances which can be made to boil at 100°C or below.

SUMMARY OF THE INVENTION

It has now been found that aromatic compounds, including those having high vapor pressures, can be sulfonated by processes in accordance with the present invention in a manner which is readily controllable and comparatively easy to operate on a commercial scale to yield a reaction product from which it is readily possible to isolate sulfonic acids or sulfonates of relatively high purity, yet without any significant problem of disposal of excess sulfuric acid.

In the process of the present invention a solvent is used, and it is the solvent which boils to remove the heat of the reaction, so that it becomes possible to sulfonate any aromatic substance provided this is susceptible to the direct action of sulfur trioxide, so as in this way to yield a product having a sulfonated aromatic nucleus, and provided of course that the aromatic compound is otherwise substantially inert to the action of sulfur trioxide under the conditions of the process. Thus, the process of the present invention is applicable not only to substances which boil under a pressure of 0.1 mm Hg at 100°C or below but also to aromatic substances that cannot be conveniently made to boil at 100°C, and thus the process can be used to sulfonate materials such as dodecyl benzene, the sulfonate of which is important in the detergent industry.

Accordingly this invention provides a process for the sulfonation of aromatic substances selected from the group consisting of aromatic compounds and mixtures thereof, said aromatic compounds being compounds susceptible to the direct action of sulfur trioxide to yield a product having a sulfonated aromatic nucleus, but otherwise substantially inert under the reaction conditions to sulfur trioxide, wherein:

1. said aromatic substance is admixed with an organic material substantially inert to the action of sulfur trioxide under the reaction conditions to be employed, so as to form a reactant which at a temperature of 100°C or below forms a liquid selected from the group consisting of liquid solutions and liquid suspensions and mixtures thereof and which boils at a temperature selected from the group consisting of 100°C and temperatures below 100°C under a pressure of 0.1 mm Hg 2. said reactant is brought to boiling in a reaction chamber at a temperature selected from the group consisting of 100°C and temperatures below 100°C under a pressure of from 0.1 mm Hg to atmospheric pressure (normally about 760 mm Hg);

3. gaseous sulfur trioxide is introduced into the boiling liquid mixture within the reaction chamber to react exothermically with the aromatic substance, heat liberated in the exothermic sulfonation reaction causing the mixture to continue to boil and furnishing the latent heat of volatilization of the matter that volatilizes 4. the matter thus volatilized is reconverted to liquid in a heat-exchanger, so that the latent heat of volatilization is given up in the heat-exchanger and heat liberated in the sulfonation reaction is thus removed from the reaction chamber;

5. the volatilized matter reconverted to liquid in the heat-exchanger is recycled to the reaction chamber; and 6. the pressure in the reaction chamber and the rate at which the gaseous sulfur trioxide is introduced into the mixture within the reaction chamber are so controlled that matter is volatilized, reconverted to the liquid state and recycled to the reaction chamber at a rate as to ensure that there is always present in the mixture within the reaction chamber an amount of volatilizable matter exceeding that amount capable of being volatilized by the heat of reaction of the aromatic substance present with the gaseous sulfur trioxide in contact with said aromatic substance in the reaction chamber and that the temperature of the mixture does not exceed a temperature selected from the group consisting of 100°C and temperatures below 100°C.

The processes of the present invention are applicable to the sulfonation of any aromatic substance (which term includes both single aromatic compounds and mixtures of two or more such compounds, and includes compounds and mixtures of compounds selected from the group consisting of compounds having a fully conjugated ring system and heterocyclic compounds which, although not possessing a fully conjugated ring system, nevertheless have a substantial degree of aromatic character) provided naturally that the aromatic substance is susceptible to the direct action of sulfur trioxide to yield a product having a sulfonated aromatic nucleus, and is otherwise substantially inert to the action of sulfur trioxide under the conditions of the process.

It is believed to be well within the competence of any chemist to determine whether any particular compound meets these requirements. Aromatic substances which would themselves boil at temperatures of 100°C or less under a reduced pressure of 0.1 mm Hg can of course be sulfonated by the process of this invention. Such relatively low-boiling aromatic compounds and substances can however equally and perhaps more conveniently be sulfonated by the process of copending Application Ser. No. 411,054 of even date herewith, which however cannot be used to sulfonate high-boiling aromatic compounds which cannot be made to boil, even under a pressure as low as 0.1 mm Hg, at a temperature of 100°C or below. It is moreover obviously and advantage of the process of this invention that it can be used to sulfonate all aromatic substances susceptible to sulfonation in the aromatic nucleus by sulfur trioxide and otherwise substantially inert to sulfur trioxide under the conditions of the process.

An aromatic compound to be susceptible to sulfonation by the process of this invention must include the group

in the aromatic nucleus, and the aromatic substances most frequently sulfonated by the process of this invention will be selected from the group consisting of aromatic compounds and mixtures thereof, said aromatic compounds being represented by the formula:

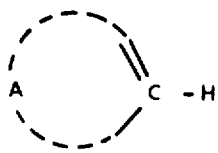

wherein A represents the remainder of an aromatic ring system selected from the group consisting of aromatic hydrocarbons, thiophene and substituted derivatives of aromatic hydrocarbons and thiophene wherein all the substituent groups are substantially inert to the action of sulfur trioxide at a temperature at which sulfonation of the aromatic nucleus can be effected by sulfur trioxide.

While a very large number of aromatic compounds may be sulfonated by the processes of the present invention, the most important classes of aromatic compounds for most industrial purposes are one-ring and two-ring hydrocarbon systems (e.g. benzene and naphthalene) and thiophene, as well as substituted derivatives of all these compounds.

Hence, the sulfonation process of the present invention is particularly applicable to aromatic substances selected from the group consisting of aromatic compounds and mixtures thereof, said aromatic compounds being represented by the formula:

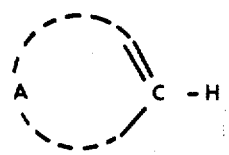

wherein A' represents the remainder of an aromatic ring system selected from the group consisting of benzene, naphthalene, thiophene, and substituted derivatives of benzene, naphthalene and thiophene wherein all the substituent groups are selectively inert to the action of sulfur trioxide at a temperature at which sulfonation of the aromatic nucleus can be effected by sulfur trioxide.

Any aromatic substance may be sulfonated by the process of this invention provided that it conforms to the requirements that it is susceptible to the direct action of sulfur trioxide to yield a product having a sulfonated aromatic nucleus and is otherwise substantially inert to the action of sulfur trioxide under the conditions of the process. However, for general guidance, it may be said that aromatic substances particularly suitable for sulfonation by the process of the invention are those selected from the group consisting of aromatic compounds and mixtures thereof, said aromatic compounds being compounds containing from 1 to 14

1 carbon atom is taken as 1 carbon-equivalent
1 fluorine atom is taken as 1 carbon-equivalent
1 chlorine atom is taken as 2 carbon-equivalents
1 bromine atom is taken as 3 carbon-equivalents
1 iodine atom is taken as 6 carbon-equivalents
1 —O— radical is taken as 1 carbon-equivalent
1 —S— radical is taken as 2 carbon-equivalents radicals where C is a carbon atom of an aromatic nucleus, selected from the group consisting of compounds containing from 6 to 24 carbon atoms and compounds containing from 6 to 24 carbon-equivalents where 1 $NO_2$ radical is taken as 6 carbon-equivalents and represented by a formula selected from the group consisting of formulae I, II, III, IV and V below:

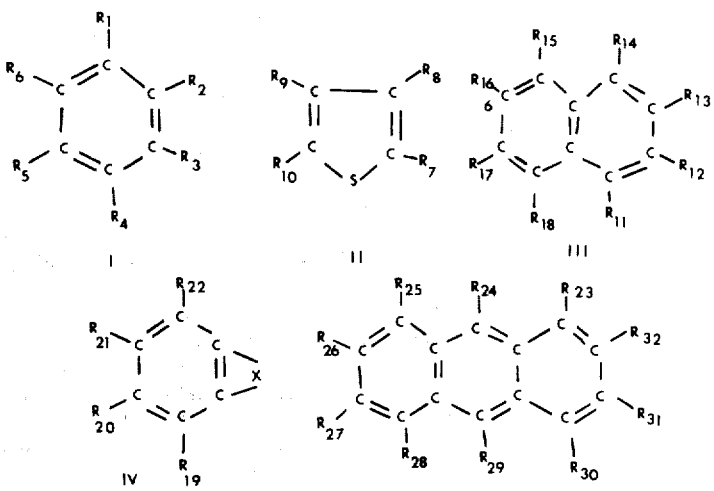

where the radicals $R_1 - R_{32}$ are selected from the group consisting of $NO_2$, F, Cl, Br, I, alkyl containing 1 – 18 carbon atoms, phenyl, alkyl-phenyl where the alkyl group contains 1 – 12 carbon atoms, phenyl-alkyl where the alkyl group contains 1 – 12 carbon atoms, phenoxy, alkyl-phenoxy where the alkyl group contains 1 – 11 carbon atoms, phenoxy-alkyl where the alkyl group contains 1 – 11 carbon atoms, alkyl-phenyl-alkyl where the alkyl groups contain in all 1 – 12 carbon atoms and H, and where X is selected from the group consisting of saturated aliphatic hydrocarbon radicals containing 4 – 18 carbon atoms and alkoxy substituted saturated aliphatic hydrocarbon radicals containing in all 4 – 17 carbon atoms, and 3 – 4 of the carbon atoms in X together with the two carbon atoms of the aromatic nucleus to which X is joined to form a ring selected from the group consisting of 5-membered rings and 6-membered rings.

Examples of compounds within Formula I above are:
benzene, toluene, ethyl-benzene, fluorobenzene, chlorobenzene, bromobenzene, iodobenzene, nitrobenzene, pentamethyl-benzene, octyl-benzene, cumene, pseudo-cumene, para-cymene, mesitylene, anisole, phenetole, dodecyl benzene, octadecyl-benzene and phenoxy-decane and all isomeric forms of xylene, ethyl-toluene, monofluorotoluene, monochloro-toluene, monobromotoluene, monoiodotoluene, dichlorobenzene, trichlorobenzene, tetrachlorobenzene, tetrafluorobenzene, dibromobenzene, diethoxybenzene, nitrotoluene, monochloro-toluene, monobromotoluene, monobromoxylene, dibromoxylene, dibromotoluene, monoiodotoluene, monoiodoxylene, monochlorophenetole, mononitrocumene, mononitroanisole, monochloro-mononitro-benzene, dinitrotoluene, dinitroxylene, di-iodo-xylene and monoiodo-mononitro-xylene.

Examples of compounds within Formula II above are: thiophene and all isomeric forms of methylthiophene, dimethylthiophene, ethyl thiophene, octyl thiophene, monochlorothiophene, monobromothiophene, monoiodothiophene, monofluorothiophene, dichlorothiophene, trichlorothiophene, trifluorothiophene, mononitrothiophene, methoxy-thiophene, heptoxy-thiophene, dodecyl thiophene, octadecyl-thiophene, dinitrothiophene and monoiodo-mononitro-thiophene.

Examples of compounds within Formula III above are:

naphthalene and all isomeric forms of methylnaphthalene, monofluoronaphthalene, monochloro-naphthalene, dimethylnaphthalene, ethyl naphthalene, monochloromethylnaphthalene, monochloro-ethylnaphthalene, methyl ethyl naphthalene, isopropyl-naphthalene, diethyl-naphthalene, dinitronaphthalene, mononitro-monoiodo-naphthalene, dibutyl-naphthalene, di-isopropylnaphthalene, decyl naphthalene and tetradecylnaphthalene.

Examples of compounds within Formula IV above are:

tetrahydronaphthalene and indane and all isomeric forms of methyltetrahydronaphthalene, ethyltetrahydronaphthalene, monofluorotetrahydronaphthalene and monochlorotetrahydro-naphthalene (the fluorine or chlorine atom in the two last-named compounds being attached to a carbon atom in the aromatic ring), methoxytetrahydronaphthalene, ethoxytetrahydronaphthalene, dimethoxytetrahydronaphthalene, mononitrotetrahydronaphthalene and dinitrotetrahydro-naphthalene (the nitro group in the last-named compounds being attached to the aromatic nucleus), dibutyltetrahydronaphthalene, decyltetrahydronaphthalene, tetradecyl-tetrahydronaphthalene, methyl-indane, pentyl-indane, pentadecyl-indane and monochloro-indane and monobromo-indane (the chlorine or bromine atom in the two last-named compounds being attached to a carbon atom in the aromatic ring).

Examples of compounds within Formula V above are:

anthracene and all isomeric forms of nitroanthracene, monochloro-anthracene, dichloroanthracene, decyl-anthracene and diethyl-anthracene.

It is not necessary for the aromatic compound which is to be sulfonated by the process of the present invention to be pure. Not only can mixtures of different aromatic compounds be employed as the aromatic substance, in the manner already indicated, but it is also frequently convenient to use commercially available aromatic materials which are mixtures of different isomers. It will also frequently be convenient to use commercially available aromatic substances which contain impurities, although it is obvious that it is generally undesirable for the aromatic substance to contain substantial quantities of unsulfonatable impurities which are likely to impair the usefulness of the end product of the sulfonation procedure, or to contain impurities which will react with the sulfur trioxide to produce tar or other undesirable products.

In the first step of the process of this invention the aromatic substance to be sulfonated must be admixed with an organic material, substantially inert to the action of sulfur trioxide under the reaction conditions to be employed, so as to form a reactant which is liquid, and indeed is capable of boiling, at a temperature of 100°C or below. This organic material will frequently be itself a liquid at ordinary ambient temperatures, and may often dissolve the aromatic substance to be sulfonated. Hennce in this specification and claims it is sometimes for convenience referred to as an organic solvent. However the organic material chosen does not necessarily need to be liquid at ambient temperatures, nor does it have to dissolve the aromatic substance.

Actually in fact, any organic substance may be used provided that after admixture with the aromatic substance to be sulfonated the resultant reactant boils under a pressure of 0.1 mm at 100°C or below, and naturally also provided is substantially inert to the action of sulfur trioxide under the conditions of the process. Unlike the process of the prior art where sulfur trioxide is used with an inert liquid diluent, it is not necessary in the process of the present invention for the organic solvent to dissolve the sulfur trioxide. Normally it is preferable for the aromatic substance to be sulfonated to form a homogeneous mixture with the organic solvent at the reaction temperature, and thus preferable for the organic solvent to dissolve the aromatic substance or vice versa. In many instances, when sulfonating one of the aromatic substances herein disclosed as suitable, using one of the preferred solvents at a temperature in the preferred range of 20° - 80°C, a homogeneous liquid will be obtained at the reaction temperature. However, it is not essential for a homogeneous liquid to be obtained; and the process can be successfully operated where there are two or more phases in the reaction chamber, because in general the ebullition as the reaction mixture boils will agitate the mixture, thus mixing the phases. Thus references hereinafter to "solvent" should be interpreted to mean a substance which, at the reaction temperature, will dissolve or disperse in the aromatic substance to be sulfonated and/or in which the aromatic substance to be sulfonated will dissolve or disperse.

As already indicated the organic solvent used may be any organic substance which is substantially inert to the action of sulfur trioxide under the reaction conditions and boils under a pressure of 0.1 mm at 100°C or below. Thus mixtures of two or more organic substances may be used, whether or not some of the components of this mixture boil undr a pressure of 0.1 mm Hg at a temperature above 100°C, provided that the mixture boils under a pressure of 0.1 mm Hg at a temperature of 100°C or below — and naturally also provided that all the components of the mixture are substantially inert to the action of sulfur trioxide under the reaction conditions. It is preferred that the solvent shall boil at the chosen sulfonation temperature without significant decomposition.

It is believed to be well within the skill of any competent chemist to determine which organic solvents meet these requirements. However for guidance it may be said the preferred organic solvents are organic substances selected from the group consisting of organic compounds and mixtures thereof said organic compounds being compounds selected from the group consisting of organic compounds containing 3 – 16 carbon atoms and organic compounds containing 3 – 16 carbon-equivalents, where:

1 carbon atom is taken as 1 carbon-equivalent 1 fluorine atom is taken as 1 carbon-equivalent
1 chlorine atom is taken as 2 carbon-equivalents
1 bromine atom is taken as 3 carbon-equivalents
1 iodine atom is taken as 6 carbon-equivalents
1 —O— radical is taken as 1 carbon-equivalent
1 NO₂ radical is taken as 6 carbon-equivalents
said compounds being also selected from the group consisting of saturated aliphatic hydrocarbons, saturated halogen-substituted aliphatic hydrocarbons containing 1 – 10 halogen atoms, saturated nitro-substituted aliphatic hydrocarbons containing 1 – 2 nitro radicals, saturated aliphatic chains containing 1 – 2 —O— linkages in an otherwise hydrocarbon chain, saturated halogen-substituted aliphatic chains containing 1 – 2 —O— linkages and 1 – 6 halogen atoms in an otherwise hydrocarbon chain, and hexa-substituted aromatic hydrocarbons wherein the substituent groups are selected from the group consisting of fluorine, methyl and ethyl.

In addition to the aromatic hydrocarbons referred to above, it is in fact possible under certain conditions to employ other aromatic hydrocarbons as the whole or a part of the solvent even if they contain one or more

groupings in the aromatic nucleus, provided naturally that they can be made to boil under a pressure of 0.1 mm Hg at a temperature of 100°C or below and that they either do not react with sulfur trioxide under the chosen conditions of the process or at least react therewith only very slowly because one or more of the substituent groupings present inhibit or retard the sulfonation reaction. Thus even aromatic substances which may themselves be sulfonated by the process of the invention but which sulfonate only slowly (e.g. para-xylene, nitro-benzene, all isomers of nitro-toluene and nitro-xylene) may be used as solvent in the process when sulfonating other more readily and more rapidly sulfonatable aromatic substances. Naturally in such circumstances a minor amount of the material used as solvent may itself be converted to the corresponding sulfonic acid, but this is usually acceptable. As an example para-xylene may conveniently be used as the solvent when sulfonating naphthalene by the process of this invention.

It is not necessary for the solvent to be pure. Mixtures of individually suitable solvents will often be employed, and it is also quite possible to use solvents or solvent mixtures containing impurities provided that such impurities are substantially inert to the action of sulfur trioxide under the reaction conditions and do not remain in the sulfonic acid or sulfonate produced by the process to such an extent as to impair its properties.

The sulfonation must be carried out at 100°C or below, and it is preferred to carry out the sulfonation at temperatures in the range of from 20°C to 80°C, temperatures from 40°C – 60°C being especially preferred. A number of suitable solvents boil at atmospheric pressure, and thus when using such solvents the process may be operated at atmospheric pressure, thus at or about 760 mm Hg. However, it is preferred to operate the process under reduced pressure, as the sulfur trioxide gas can then conveniently be sucked or aspirated into the reaction mixture. When operating at atmospheric pressure the sulfur trioxide must be forced in under pressure, which is less convenient. The process may be operated at a pressure as low as 0.1 mm Hg, but it is preferred to work under pressures ranging from 3 – 700 mm Hg, and pressures of 25 – 400 mm Hg are most convenient.

Thus the preferred solvents are those which boil at 20° – 80°C under a pressure of 3 – 700 mm Hg, and especially those which boil at 40° – 60°C under a pressure of 25 – 400 mm Hg.

Examples of particularly preferred solvents are n-hexane, cyclohexane, n-haptane, n-octane and mixtures of two or more of these. Examples of other suitable solvents are n-butane, n-pentane, n-decane, n-hexadecane and all other isomers of butane, pentane, decane and hexadecane, as well as nitro methane, dinitrobutane (all isomers), tetrachloro-ethane (1,1,2,2), carbon tetrachloride, dichloro-difluoro-ethane (all isomers), penta-chloro-ethane, hexafluoro-hexane (all isomers), hexamethyl-benzene, ethyl-penta-methyl-benzene, monochloro-penta-methyl-benzene, mono-fluoro-penta-methyl-benzene, diethyl ether, dioxane, dibutyl ether (all isomers), dihexyl ether (all isomers), tetrahydrofurfuran, dichloro-diethyl-ether (all isomers), difluoro-diethyl-ether (all isomers), tetrafluoro-dibutyl ether (all isomers) and hexa-chloro-diethyl ether (all isomers).

Saturated aliphatic hydrocarbons and aromatic hydrocarbons inert to sulfur trioxide are preferred, as the other solvents referred to above tend to be less stable under the reaction conditions. For instance, the chlorinated solvents may break down in the process to some extent, in some cases producing phosgene which is toxic and undesirable.

The ratio of solvent to aromatic substance to be sulfonated may be varied considerably. As little as 1% by weight of the solvent calculated on the aromatic substance to be sulfonated may be used, or even less. If the aromatic substance to be sulfonated also boils at the reaction temperature, it may then be unnecessary to use a substantial percentage of the solvent; and even when the aromatic substance does not boil or vaporize to a significant extent at the reaction temperature, it is still possible to use only a small percentage of the solvent, even as little as 1% by weight of solvent calculated on the aromatic substance to be sulfonated. However, it is essential to keep an amount of volatilizable matter in the reaction chamber which exceeds that amount capable of being volatilized by the heat of reaction of the aromatic substance present with the gaseous sulfur trioxide in contact with the aromatic substance in the reaction chamber. Clearly this will be difficult to achieve if the solvent is the only volatilizable material present, and only very little of the solvent is present; and in such circumstances it is necessary for the sulfur trioxide to be passed only very slowly into the reaction mixture, so that the rate of sulfonation will therefore be slow. On the other hand, it is not convenient to use a very large excess of solvent as this all has to be distilled off at the end of the reaction or removed from the reaction product in some other way. In general it is preferred to use from 1% to 1000% of solvent by weight calculated on the aromatic substance to be sulfonated, and it is especially preferred to use from 20% to 200% by weight.

In the process of the aforesaid co-pending Application Ser. No. 411,054 it is necessary to have present an excess of the aromatic substance during the entire reaction, as this aromatic substance is required to boil so as to remove the heat of the reaction. In the present process however, it is not necessary for an excess of the aromatic substance to remain until the end of the reaction, and it is possible the amount of sulfur trioxide passed during the process to be sufficient or nearly sufficient to convert the whole of the aromatic substance present to the sulfonic acid. Conveniently sufficient sulfur trioxide may be employed to react with from 90% to 100% of the aromatic substance present, and in such cases it is necessary to stop the flow of sulfur trioxide into the reaction mixture when the desired degree of conversion of the aromatic substance to the corresponding sulfonate has been achieved. If it is desired to convert all the aromatic substance present to sulfonate, it is of course possible to pass an excess of sulfur trioxide, but on a commercial scale this generally will not be convenient, as it means that sulfur trioxide will escape from the reaction chamber, and clearly it is undesirable that this should pass into the atmosphere. Therefore when it is desired to sulfonate all or substantially all of the aromatic substance present, it will generally be necessary carefully to measure the amount of sulfur trioxide passed. It is naturally possible to employ an excess of the aromatic substance and this may often be convenient especially when the aromatic substance is volatile and can conveniently be distilled, if necessary under reduced pressure. The excess employed when operating the process as a batch process will often conveniently be from 1% to 100% by weight above that theoretically needed to react with the sulfur trioxide used in the process. When using an excess of aromatic substance it is however unnecessary to use accurately weighed or measured proportions of the reactants, so long as an excess of the aromatic substance is present in the reaction chamber at all times while the sulfur trioxide is passed. The fact that it is not necessary accurately to control the proportions of the reactants is especially convenient when the reaction is conducted as a continuous process, since it eases the technical problems of measuring and controlling the sulfur trioxide stream. The use of an excess of the aromatic substance also minimizes undesirable sulfone formations. Even by this process however some sulfone may be produced, and a sulfone depressor (for example acetic acid or acetic anhydride) may be incorporated into the reaction mixture so as to reduce sulfone formation.

In the present process it is essential that some solvent and/or some volatile aromatic substance shall be present during the entire reaction. Inevitably therefore the finished product will comprise the desired aromatic sulfonic acid (together with any unreacted aromatic substance and certain impurities) and usually with a quantity of the solvent employed.

If no significant excess of the aromatic substance has been employed the end-product of the reaction will generally comprise the desired sulfonic acid and the solvent, together with a comparatively minor amount of unreacted aromatic substance and by-products of the reaction. The solvent may be conveniently removed by distillation, preferably under reduced pressure, leaving the aromatic sulfonic acid together with the unreacted aromatic substance and by-products of the reaction. In many cases the aromatic sulfonic acid will, when the solvent has been removed, be sufficiently pure for it to be used commercially without further purification.

If an excess of aromatic substance has been employed, then the end-product of the reaction will generally comprise the desired sulfonic acid (together with any by-products of the reaction), excess aromatic substance and the solvent. In many instances, the latter two materials are conveniently removed together from the reaction product, and simply recycles in the process adding additional aromatic substance to the mixture in order to replace that aromatic substance which has been converted to sulfonate. In a continuous process it will normally be convenient to use an excess of aromatic substance, and recycle the mixture of aromatic substance and solvent, adding additional aromatic substance as necessary in the manner described.

If the aromatic substance and the solvent are both readily volatile (if necessary under reduced pressure) they may be distilled off together from the sulfonic acid and reaction by-products. Anhydrous sulfonic acids of over 95% purity can be obtained in this way. Alternatively water or aqueous solutions of alkali may be added, with cooling, to the reaction product, and the mixture will frequently separate on standing into two phases. If the relative density of the mixture of the unreacted aromatic substance and solvent is less than the relative density of the aqueous solution of sulfonic acid or sulfonate which has been formed, then the top layer will contain the solvent and aromatic substance. The two layers can then be separated. The lower layer will contain the desired sulfonic acid or sulfonate salt, and this layer may be boiled — preferably under reduced pressure — to remove any remaining solvent and, if it is sufficiently volatile, any unreacted aromatic substance. This latter method removes from the sulfonic acid or sulfonate solution most of the sulfone, whose formation always to some extent accompanies the production of sulfonic acids by sulfonation with sulfur trioxide. The other layer containing the unreacted aromatic substance and solvent may then be recycled in the process of the invention after drying, and if necessary after purification, e.g. by distillation.

The sulfur trioxide employed in the process of the invention may be provided in any convenient way. While the use of sulfur trioxide diluted with air or another inert gas is not excluded, this could give rise to entrainment losses which will become more and more unacceptable as the degree of dilution increases. Hence no advantage is usually seen in diluting the sulfur trioxide, which therefore should normally be used undiluted, thus in the state of purity in which it is commercially available. Thus the sources of sulfur trioxide may conveniently be either commercially available stabilized sulfur trioxide or oleum. The sulfur trioxide thus generated may conveniently be merely aspirated into the aromatic substance.

It has been found that the absorption of sulfur trioxide in the process of the present invention is almost quantitative in the liquid phase. If however the aromatic substance volatilizes during the process, the liquid aromatic substance returning to the reaction chamber from the heat-exchanger will effect a further scrubbing of any gaseous sulfur trioxide which may have escaped from the reaction chamber.

Naturally, any solvent or aromatic compound recovered may be recycled in the process of the invention, if necessary after purification by distillation.

Where it is possible to do so, it is preferred to operate the process continuously, by feeding the aromatic substance and the substantially inert organic material continuously into the reaction chamber there to form a boiling liquid reactant, introducing the sulfur trioxide continuously into the boiling mixture within the reaction chamber, withdrawing reaction mixture continuously from the reaction chamber, separating both the unreacted aromatic substance and the inert organic material from the unreacted aromatic substance, and purifying the former and recycling them in the process.

The invention also extends to any aromatic sulfonic acid and the salts thereof whenever the sulfonic acid is prepared by the sulfonation process of this invention.

DETAILED DESCRIPTION OF THE INVENTION

The invention will now be described, though only by way of illustration, with reference to the apparatus shown in the accompanying drawings. Details of preferred reagents, conditions and techniques employed in the process of the present invention are given in the Example which follows the description with reference to the drawings.

General batch production.

Figure 1:
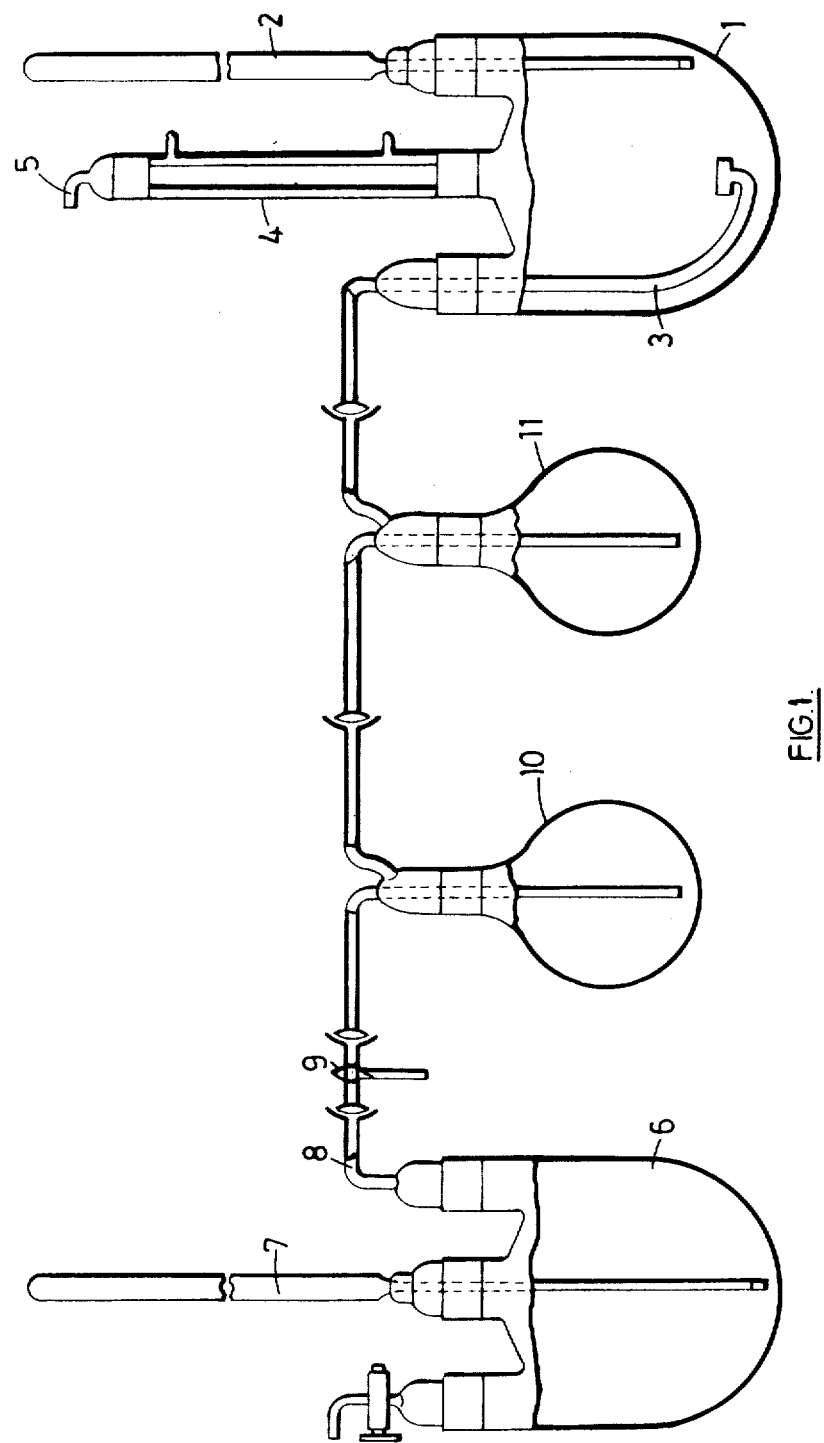

An apparatus for carrying out a reaction batchwise in accordance with the present invention is illustrated in FIG. 1 of the accompanying drawings. In this apparatus, a three-necked flask is employed as the reaction vessel, and is fitted with a thermometer 2, a gas inlet tube 3 reaching to the bottom of the flask and a reflux condenser 4 which is connected to a vacuum pump by the line 5. A two-necked flask 6, fitted with a thermometer 7 and a vapor oulet line 8, is provided as sulfur trioxide generator. The two flasks are connected through a tap unit 9 and two empty flasks 10 and 11 which serve as safety traps.

The approximate amount of the dry aromatic substance to be sulfonated is placed in the reaction vessel 1 together with the appropriate quantity of the solvent, and the appropriate quantity of sulfur trioxide in liquid stabilized form is placed in the flask 6. The aromatic substance and solvent are then heated to the desired reaction temperature and, on reduction of the pressure, matter begins to reflux. The sulfur trioxide generator heated to a predetermined temperature is then connected via the tap 9 to the reactor 1 through the vapor line of the generator and the gas inlet line of the latter. Sulfur trioxide evaporates into the partially-evacuated system and passes into the boiling reaction mixture which remains vigorously agitated by ebullition throughout the reaction. Gentle warming of the trioxide generator is maintained throughout the reaction to aid evaporation. The reaction vessel itself need not be heated at all since the strongly exothermic reaction maintains the mixture at the boil whilst any excess heat of reaction is removed as latent heat of volatilization.

The reaction is completed when all the sulfur trioxide has evaporated and passed from the generator into the reaction mixture. At the same time reflux ceases as no further heat is evolved.

General continuous production.

Figure 2:
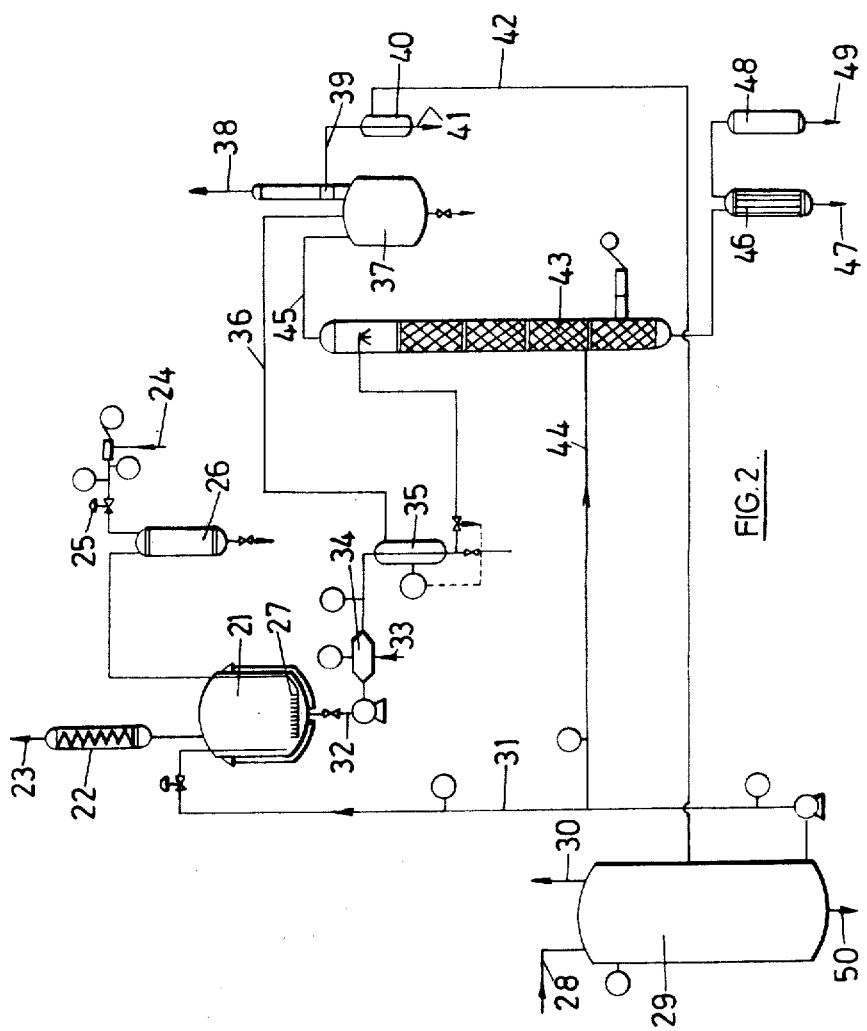

A plant for carrying out a process of the present invention for the sulfonation of a volatile aromatic substance in a continuous manner using a volatile hydrocarbon solvent having a relative density of less than 1 is illustrated in FIG. 2 of the accompanying drawings.

In this plant a reactor 21 is provided with a reflux condenser 22 itself attached to a vacuum line 23. Sulfur trioxide is supplied via a line 24 regulated by a tap 25 to an evaporator 26 and thence to a gas inlet nozzle 27 at the base of the reactor 21. The aromatic substance to be sulfonated is mixed with the solvent, and the mixture is supplied from bulk storage via a line 28 to a feed tank 29 having a safety vent 30. From this tank the mixture of solvent and aromatic substance is fed to the reactor 21 by the line 31. Reaction mixture may be continuously withdrawn from the base of the reactor by the line 32 and mixed with water or aqueous alkali fed by the line 33 in an in-line mixer unit 34 from where it passes to a separator 35 with a recycle circuit. The solvent together with unreacted aromatic substance is taken from the separator 35 as the upper layer and fed via line 35 to a distillation vessel 37 attached to a vacuum line 38. After vacuum distillation the mixture of solvent and unreacted aromatic substance is passed via the line 39 into a further separator 40 from where water is removed by the line 41 and the mixture of unreacted aromatic substance and solvent is then returned via the line 42 to the feed tank 29. As the process continues the percentage of solvent in the feed tank 29 will increase and further aromatic substance unadmixed with solvent must be added to maintain the desired ratio of solvent to aromatic substance.

The aqueous sulfonic acid of sulfonate solution is fed from the separator 35 to the top of an extraction column 43, into the middle of which is passed some of the mixture of solvent and aromatic substance taken by a line 44 from the supply line 31. The mixture of solvent and aromatic compound removed overhead from the extraction column is passed by line 45 to the distillation vessel 37. The aqueous sulfonic acid or sulfonate is led from the base of the extraction column 43 to a stripper 46 from which the final traces of solvent and unreacted aromatic substance are removed and the pure final product is then removed from the plant by a line 47. The small quantities of water, solvent and unreacted aromatic substance removed in this final stripper 46 are condensed in vessel 48 and then recycled via line 49. Some water is also contained in the recycle line 42, and this accumulates at the bottom of the feed tank 29 from which it may be removed by the drain plug 50.

EXAMPLE 1

In the apparatus described in FIG. 1 nitrobenzene was sulfonated. Dry nitrobenzene (246 g, 2 gram-molecules) containing acetic acid (1 g) was diluted with cyclo-hexane (100 g) previously washed with concentrated sulfuric acid to remove any trace of unsaturated or oxidized material. The sulfonation was conducted at 40°C under a pressure of 500 mm Hg by aspirating into the refluxing mixture sulfur trioxide (80 g, 1 gram-molecule) in vapor form. After completion of the reaction m-nitrobenzene sulfonic acid was isolated as a deep yellow 50% aqueous solution by the addition of water (200 g). The aqueous solution was briefly boiled to remove and recover by steam distillation excess nitrobenzene and cyclohexane solvent. The recovered excess nitrobenzene and solvent are suitable for re-use after drying.

Each of the following compounds may be reacted with sulfur trioxide (using the reactants in the proportion of 2 gram-molecules of the compound to 1 gram-molecule of the sulfur trioxide) by the procedure given above by substituting the solvent named in each case for the cyclohexane used in the Example, making in each case appropriate adjustment of the pressure to ensure that the mixture of solvent and aromatic substance boils at a temperature of from 20° to 80°C. (The amount of solvent used need not be the same as in the Example above, but may vary from 30% to 200% by weight, calculated on the amount of aromatic substance used).

| Aromatic substance | solvent |
|---|---|
| Benzene | n-pentane |
| Thiophene | n-pentane |
| Bromobenzene | cyclohexane |
| Toluene | n-heptane |
| ortho-Xylene | n-hexane |
| Meta-Xylene | 1,1,2,2-tetrachloroethane |
| Anisole | diethyl ether |

The following substances may be sulfonated by a similar procedure, using in each case the standard solvent but using 0.9 to 1.0 gram-molecules of sulfur trioxide to 1 gram-molecule of the aromatic substance, and in each case making appropriate adjustment of the pressure to ensure that the mixture of solvent and aromatic substance boils at a temperature of from 20° to 100°C.

| Aromatic substance | Solvent |
|---|---|
| Naphthalene | dioxane |
| Nitro-naphthalene | iso-heptane |
| Anthracene | methyl cyclohexane |
| Tetrahydro-naphthalene | nitromethane |

I claim:
1. A process for the sulfonation of aromatic compounds selected from the group consisting of benzene, thiophene, bromobenzene, toluene, ortho-xylene, meta-xylene, anisole, naphthalene, nitro-naphthalene, anthracene and tetrahydro-naphthalene, wherein:
　1. said aromatic compound is admixed with an organic solvent substantially inert to the action of sulfur trioxide under the sulfonation conditions to form a liquid mixture, and said organic solvent is admixed in a quantity of from 20% to 200% by weight based on the weight of aromatic compound, and said organic solvent is selected from the group consisting of n-pentane, n-hexane, n-heptane, iso-heptane, cyclohexane, methylcyclohexane, diethyl ether, dioxane, nitromethane and 1,1,2,2-tetrachloroethane;
　2. The liquid mixture is brought to boiling in a reaction chamber at a temperature of from 20°C to 100°C at a pressure of 0.1 mm Hg to atmospheric pressure;
　3. gaseous sulfur trioxide is introduced into the boiling liquid mixture within the reaction chamber to react exothermically with the aromatic compound, said aromatic compound being employed in an excess quantity to maintain the constant presence of some unreacted aromatic compound in the reaction chamber during the sulfonation reaction, heat liberated in the exothermic sulfonation reaction causing the mixture to continue to boil and furnishing the latent heat of volatilization of the matter that volatilizes;
　4. the matter thus volatilized is reconverted to liquid in a heat-exchanger, so that the latent heat of volatilization is exchanged in the heat-exchanger and heat liberated in the sulfonation reaction is thus removed from the reaction chamber;
　5. the volatilized matter reconverted to liquid in the heat-exchanger is recycled to the reaction chamber; and
　6. the pressure in the reaction chamber and the rate at which the gaseous sulfur trioxide is introduced into the liquid mixture within the reaction chamber are so controlled that matter is volatilized, reconverted to the liquid state and recycled to the reaction chamber at such a rate as to ensure that there is always present in the mixture within the reaction chamber an amount of volatilizable matter exceeding that amount capable of being volatilized by the heat of reaction of the aromatic compound present with the gaseous sulfur trioxide in contact with said aromatic compound in the reaction chamber and that the temperature of the reaction mixture is from 20°C to 100°C.

2. A process according to claim 1, in which the pressure in the reaction chamber when the sulfur trioxide is introduced into the liquid mixture within the reaction chamber is from 25 to 400 mm Hg.

3. A process according to claim 1, in which the gaseous sulfur trioxide is introduced in substantially pure form into the liquid mixture within the reaction chamber.

4. A process according to claim 1, wherein the process is operated continuously, the aromatic compound and substantially inert organic solvent being continuously fed into the reaction chamber to form a liquid mixture, the sulfur trioxide being continuously introduced into the liquid mixture while this is boiling therein, the resultant reaction mixture being continuously withdrawn from the reaction chamber, and both the substantially inert organic solvent and the unreacted aromatic compound being separated from the sulfonated aromatic compound and purified and recycled to the reaction chamber.

* * * * *

UNITED STATES PATENT OFFICE
CERTIFICATE OF CORRECTION

Patent No. 3941810          Dated March 2, 1976

Inventor(s) Adolf Koebner

It is certified that error appears in the above-identified patent and that said Letters Patent are hereby corrected as shown below:

Column 5, in the diagram - "A" should be --A'--

Column 6, lines 1-10 are transposed - and should be inserted after lines 10-14.

Column 8, line 8 - "Hennce" should be --Hence--.

Column 8, line 17 - after "provided" insert --it--.

Column 8, line 22 - after "solvent" insert --used--.

Column 8, line 49 - "undr" should be --under--.

Column 12, line 7 - "recycles" should be --recycled--.

Column 14, line 25 - "of" should be --or--.

Column 15, line 18 - "standard" should be --stated--.

Column 16, line 16 - "the" should be --this--.

Signed and Sealed this

Twenty-fourth Day of August 1976

[SEAL]

Attest:

RUTH C. MASON
*Attesting Officer*

C. MARSHALL DANN
*Commissioner of Patents and Trademarks*